United States Patent
Doi

(10) Patent No.: US 9,900,559 B2
(45) Date of Patent: Feb. 20, 2018

(54) ENDOSCOPE SYSTEM

(71) Applicant: OLYMPUS CORPORATION, Shibuya-ku, Tokyo (JP)

(72) Inventor: Takahiro Doi, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 637 days.

(21) Appl. No.: 14/056,733

(22) Filed: Oct. 17, 2013

(65) Prior Publication Data

US 2014/0043456 A1    Feb. 13, 2014

Related U.S. Application Data

(63) Continuation of application No. PCT/JP2011/061744, filed on May 23, 2011.

(51) Int. Cl.
| | |
|---|---|
| H04N 9/47 | (2006.01) |
| A61B 1/04 | (2006.01) |
| H04N 5/253 | (2006.01) |
| H04N 7/18 | (2006.01) |
| G02B 23/24 | (2006.01) |

(Continued)

(52) U.S. Cl.
CPC ......... *H04N 7/183* (2013.01); *A61B 1/00016* (2013.01); *A61B 1/00022* (2013.01); *G02B 23/2476* (2013.01); *H04N 5/23245* (2013.01); *H04N 9/79* (2013.01); *H04N 7/185* (2013.01); *H04N 2005/2255* (2013.01)

(58) Field of Classification Search
CPC ... A61B 1/00043; A61B 1/00045; A61B 1/00; A61B 1/045; A61B 1/05
USPC .......................................................... 348/74
See application file for complete search history.

(56) References Cited

U.S. PATENT DOCUMENTS

| | | | |
|---|---|---|---|
| 2006/0176241 A1 | 8/2006 | Sampsell | |
| 2007/0223696 A1 | 9/2007 | Furuyama | |

(Continued)

FOREIGN PATENT DOCUMENTS

| | | |
|---|---|---|
| CN | 101115113 A | 1/2008 |
| JP | 2006-113558 A | 4/2006 |

(Continued)

OTHER PUBLICATIONS

International Search Report (ISR) dated Aug. 30, 2011 (and English translation thereof) issued in International Application No. PCT/JP2011/061744.

(Continued)

*Primary Examiner* — Mehrdad Dastouri
*Assistant Examiner* — Kristin Dobbs
(74) *Attorney, Agent, or Firm* — Holtz, Holtz & Volek PC

(57) ABSTRACT

An endoscope system is provided with: an endoscope apparatus capable of recording a picked-up endoscopic image; a memory card attachable to and detachable from the endoscope apparatus, the memory card transmitting the picked-up endoscopic image; and a PC or a mobile terminal having a function of communicating with the memory card and recording the endoscopic image transmitted from the memory card. The endoscope apparatus, and the PC or the mobile terminal are connected via wireless communication. When freeze processing is executed, the endoscope apparatus transmits an endoscopic image from the endoscope apparatus to the PC or the mobile terminal.

6 Claims, 10 Drawing Sheets

(51) Int. Cl.
*A61B 1/00* (2006.01)
*H04N 9/79* (2006.01)
*H04N 5/232* (2006.01)
*H04N 5/225* (2006.01)

(56) References Cited

U.S. PATENT DOCUMENTS

| | | |
|---|---|---|
| 2008/0024632 A1 | 1/2008 | Otsuka |
| 2008/0132169 A1 | 6/2008 | Muramatsu |
| 2008/0155667 A1 | 6/2008 | Hamachi |
| 2009/0179985 A1 | 7/2009 | Amling |
| 2009/0231418 A1* | 9/2009 | Higuchi .................... G06T 3/40 348/74 |

FOREIGN PATENT DOCUMENTS

| | | | |
|---|---|---|---|
| JP | 2006-155589 A | | 6/2006 |
| JP | 2008-092249 A | | 4/2008 |
| JP | 2008-178069 A | | 7/2008 |
| JP | 2008-284037 A | * | 11/2008 |
| JP | 2008-284037 A | | 11/2008 |
| JP | 2008-289725 A | * | 12/2008 |
| JP | 2008-289725 A | | 12/2008 |
| JP | 2009-165832 A | | 7/2009 |
| WO | WO 2006/049224 A1 | | 5/2006 |

OTHER PUBLICATIONS

Chinese Office Action dated Feb. 10, 2015, issued in counterpart Chinese Application No. 201180070936.6.

\* cited by examiner

ENDOSCOPE SYSTEM

CROSS REFERENCE TO RELATED APPLICATION

This application is a continuation application of PCT/JP2011/061744 filed on May 23, 2011, the entire contents of which are incorporated herein by this reference.

BACKGROUND OF THE INVENTION

1. Field of the Invention

The present invention relates to an endoscope system, and in particular to an endoscope system provided with a communication function.

2. Description of the Related Art

Conventionally, by inserting an insertion section of an endoscope apparatus into an object such as an engine and piping for aircraft, observation and examination of a scar, corrosion and the like of an examination target region in the object are performed. After such an examination, an examiner prepares an examination report and the like using endoscopic images photographed and recorded by the endoscope apparatus. In this case, the examiner has to carry the endoscope apparatus in which the endoscopic images are recorded, for example, to a company, his house or the like and has to spend much labor carrying the endoscope apparatus.

Therefore, the examiner transfers and records the endoscopic images photographed by the endoscope apparatus to a mobile device such as a personal computer (hereinafter referred to as a PC). Then, the examiner takes the mobile device back, for example, to the company, his house or the like to prepare the examination report and the like using the recorded endoscopic images.

For example, Japanese Patent Application Laid-Open Publication No. 2009-165832 discloses a technique in which an endoscope equipped with a network interface transfers uncompressed data such as digital video to a separate receiver via a communication network.

SUMMARY OF THE INVENTION

An endoscope system according to an aspect of the present invention is provided with: an endoscope apparatus capable of recording a picked-up endoscopic image; a communication device attachable to and detachable from the endoscope apparatus, the communication device transmitting the picked-up endoscopic image; and a mobile device having a function of communicating with the communication device and recording the endoscopic image transmitted from the communication device; wherein the endoscope apparatus and the mobile device are connected via wireless communication; and the endoscope apparatus transmits the endoscopic image from the endoscope apparatus to the mobile device when freeze processing is executed.

An endoscope system according to another aspect of the present invention is provided with: an endoscope apparatus capable of recording a picked-up endoscopic image; a communication device attachable to and detachable from the endoscope apparatus, the communication device transmitting the picked-up endoscopic image; and a mobile device having a function of communicating with the communication device and recording the endoscopic image transmitted from the communication device; wherein the endoscope apparatus and the mobile device are connected via wireless communication; and the endoscope apparatus has a first mode of transmitting the endoscopic image to the mobile device and a second mode of not transmitting the endoscopic image to the mobile device, creates a folder for storing the endoscopic image when the second mode is changed to the first mode, and stores the picked-up endoscopic image in the folder until the first mode is changed to the second mode.

DETAILED DESCRIPTION OF THE PREFERRED EMBODIMENTS

Embodiments of the present invention will be described in detail below with reference to drawings.

First Embodiment

First, a configuration of an endoscope apparatus of a first embodiment will be described on the basis of FIGS. 1 and 2.

Figure 1:
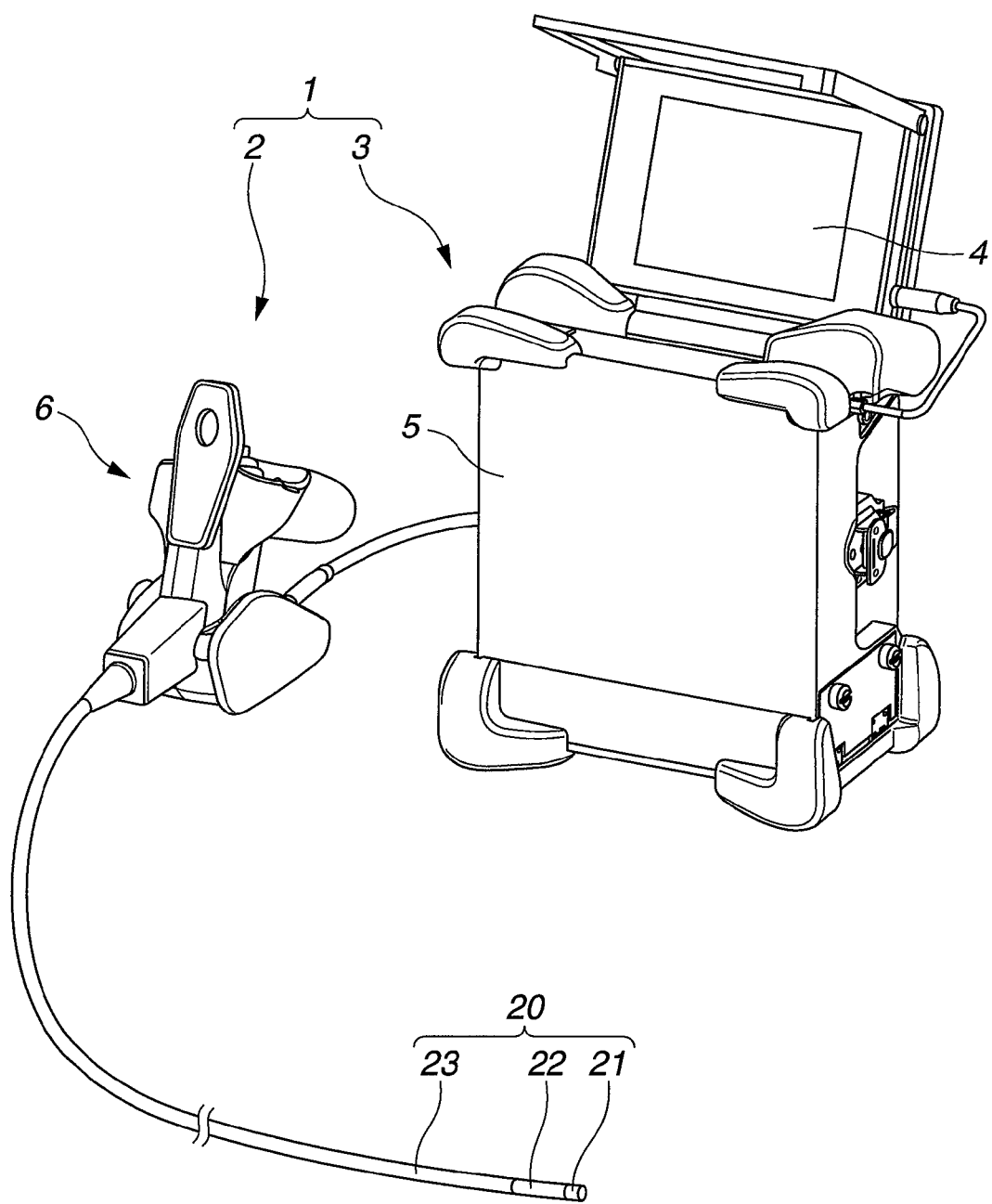
FIG. 1 is a diagram showing a whole configuration of an endoscope apparatus according to a first embodiment.
Figure 2:
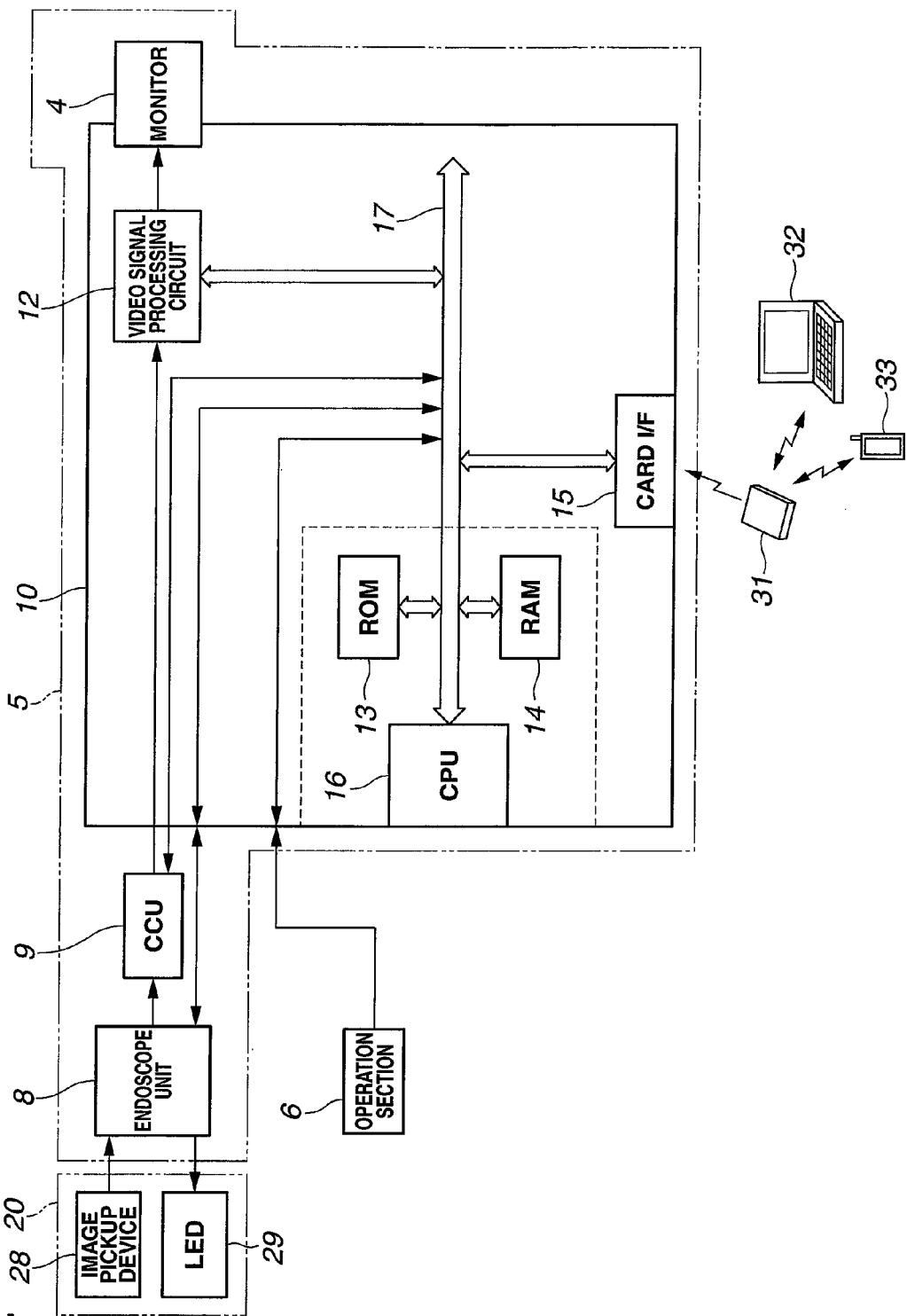
FIG. 2 is a diagram showing an internal configuration of the endoscope apparatus according to the first embodiment.

FIG. 1 is a diagram showing a whole configuration of the endoscope apparatus according to the first embodiment, and FIG. 2 is a diagram showing an internal configuration of the endoscope apparatus according to the first embodiment.

As shown in FIG. 1, an endoscope apparatus 1 is provided with an endoscope 2 and an apparatus body 3 connected to the endoscope 2. The endoscope 2 is provided with an elongated insertion section 20 and an operation section 6 for performing operations required at the time of executing various operation controls of the whole apparatus. The apparatus body 3 is provided with a monitor 4 (a liquid crystal monitor) which is a display device for displaying an image of an object picked up by the endoscope 2, operation control contents (for example, a processing menu) and the like, and a casing 5 having a control unit 10 (see FIG. 2.) inside.

The insertion section 20 is configured by arranging a rigid distal end portion 21, a bending section 22 which is bendable, for example, both up and down, left and right, and a flexible tube section 23 having flexibility sequentially and continuously from a distal end side. Various optical adapters, such as a stereo optical adapter having two observation visual fields and an optical adapter for normal observation having one observation visual field, are attachable to and detachable from the distal end portion 21. In the present embodiment, when measurement is performed, a left image and a right image, which are a pair of right and left object images, are picked up through a stereo optical adapter capable of forming two object images for the same object.

As shown in FIG. 2, an endoscope unit 8, a CCU 9 (a camera control unit) and the control unit 10 are provided in the casing 5, and a proximal end portion of the insertion section 20 is connected to the endoscope unit 8. The endoscope unit 8 is configured, being provided with a light source driving device which drives a light source (an LED 29) included in the distal end portion 21 and a bending device which bends the bending section 22 constituting the insertion section 20.

An image pickup device 28 and the LED 29 are included in the distal end portion 21. The image pickup device 28 performs photoelectric conversion of object images formed through the optical adapter to generate an image-pickup signal. The image pickup signal outputted from the image pickup device 28 is inputted to the CCU 9 via the endoscope unit 8. The image pickup signal is converted to a video signal (image data), for example, an NTSC signal or the like in the CCU 9 and provided to the control unit 10. The LED 29 generates an illumination light to be radiated to an object. Though the LED 29 is included in the distal end portion 21 in the present embodiment, the LED 29 may be arranged in the casing 5 so that an illumination light generated by the LED 29 is led to the distal end portion 21 by optical fiber. Illumination other than illumination by an LED may be used.

A video signal processing circuit 12 to which a video signal is inputted, a ROM 13, a RAM 14, a card I/F 15 (a card interface) and a CPU 16 which, on the basis of a main program, executes the various functions to perform operation control are provided in the control unit 10. The video signal processing circuit 12, the ROM 13, the RAM 14, the card I/F 15 and the CPU 16 are connected to one another via a bus 17.

Not only the CCU 9 and the endoscope unit 8 but also the operation section 6 for performing control of and giving an operation instruction to the CCU 9, the endoscope unit 8 and the like are connected to the bus 17. When a user operates the operation section 6, content of the operation is provided to the CPU 16 via the bus 17. The CPU 16 controls the operation of the CCU 9 and the endoscope unit 8 on the basis of the content of the operation.

A memory card 31 can be freely attached to and detached from the card I/F 15. By attaching the memory card 31 to the card I/F 15, it becomes possible to capture data such as control processing information and image information recorded in the memory card 31 into the control unit 10 or record the data such as control processing information or image information to the memory card 31 in accordance with control by the CPU 16.

In the present embodiment, the memory card 31 is, for example, an Eye-Fi card having performance of a communication device, such as a Wi-Fi function, and is configured to be capable of storing picked-up image information and the like as well as capable of transmitting the image information and the like to a PC 32 and a mobile terminal 33 which are external apparatuses. Thus, the endoscope system of the present embodiment is configured by the endoscope apparatus 1, the memory card 31 having a function of a communication device, and a mobile terminal such as the PC 32 and the mobile terminal 33.

In order to display a composite image obtained by combining an endoscopic image based on a video signal provided from the CCU 9 and an operation menu by graphics, the video signal processing circuit 12 performs processing for combining a graphics image signal based on the operation menu, which is generated by control of the CPU 16, and the video signal from the CCU 9, processing required for performing display on a screen of the monitor 4, and the like, and provides a display signal to the monitor 4. The video signal processing circuit 12 is also capable of performing processing for merely displaying an endoscopic image or an image of the operation menu or the like alone. Therefore, an endoscopic image, an image of the operation menu, a composite image of the endoscopic image and the image of the operation menu, or the like is displayed on the screen of the monitor 4.

The CPU 16 controls various circuit sections and the like to perform processing corresponding to a purpose by executing a program stored in the ROM 13 and performs operation control of the whole endoscope apparatus 1. The RAM 14 is used by the CPU 16 as a work area for temporarily storing data.

Next, an operation of the endoscope apparatus 1 configured as described above will be described.

Figure 3:
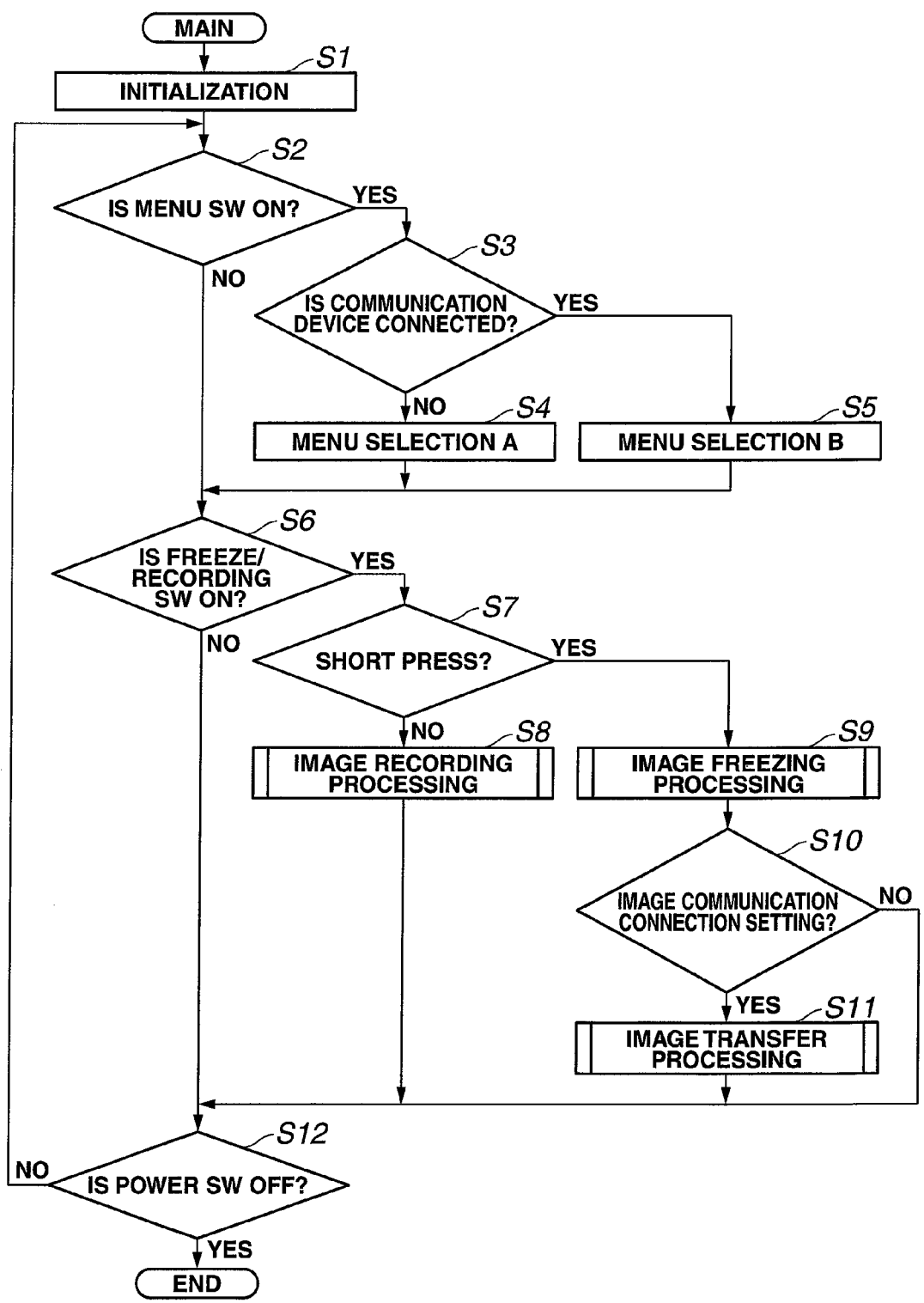
FIG. 3 is a flowchart showing an example of an operation of an endoscope apparatus 1 of the first embodiment.

FIG. 3 is a flowchart showing an example of the operation of the endoscope apparatus 1 of the first embodiment.

First, when the endoscope apparatus 1 is started, the CPU 16 executes initialization (step SI). Then, the CPU 16 monitors a signal inputted from the operation section 6 and judges whether a menu switch is on or not (step S2). If the menu switch is off, the process proceeds to step 86. On the other hand, if the menu switch is on, the CPU 16 judges whether a communication device is connected or not, specifically, whether the card I/F 15 is equipped with the memory card 31 or not (step S3). If a communication device is not connected, the CPU 16 executes menu selection A for making basic operation setting (step 84) and proceeds to step 86. On the other hand, if a communication device is connected, the CPU 16 executes menu selection B for making basic operation setting and image communication connection setting (step S5) and proceeds to step 86.

Then, the CPU 16 monitors a signal inputted from the operation section 6 and judges whether a freeze/recording switch is on or not (step S6). If the freeze/recording switch is off, the process proceeds to step S12. On the other hand, if the freeze/recording switch is on, the CPU 16 judges whether the freeze/recording switch has been short pressed or not (step S7). If the freeze/recording switch has not been short pressed, that is, the freeze/recording switch has been long pressed, the CPU 16 executes image recording processing for recording a still image and a moving image (step S8) and proceeds to step S12. On the other hand, if the freeze/recording switch has been short pressed, the CPU 16 executes image freeze processing (step S9).

Thus, in the present embodiment, the image freeze processing is executed if the freeze/recording switch provided in the operation section 6 is short pressed, and the image recording processing is performed if the freeze/recording switch is long pressed. The image recording processing includes still image recording processing and moving image recording processing. When the user long presses the freeze/recording switch provided in the operation section 6, a still image is recorded. When the user further long presses the freeze/recording switch, display for causing the user to select whether the moving image recording processing is to be performed or not is displayed on the monitor 4. Thereby, the user can select whether or not to perform the moving image recording processing, using the operation section 6. Thus, in the present embodiment, it is possible to perform three kinds of processing, the freeze processing, the still image recording processing and the moving image recording processing, using one freeze/recording switch provided in the operation section 6. Note that three switches may be provided in the operation section 6 so that the freeze processing, the still image recording processing and the moving image recording processing can be specified by the different switches, respectively.

Then, the CPU 16 judges whether the image communication connection setting has been made by the processing of step S5 (step S10). If the image communication connection setting has not been made, the process proceeds to step S12. On the other hand, if the image communication connection setting has been made, the CPU 16 executes image transfer processing for transferring images from the memory card 31 having a communication device to the PC 32 or the mobile terminal 33 (step S11) and proceeds to step S12.

Lastly, the CPU 16 monitors a signal inputted from the operation section 6 and judges whether a power switch for power source is off or not (step S12). If the power switch is off, the endoscope apparatus 1 ends the operation. On the other hand, if the power switch is on, the process returns to step S2, and a similar process is repeated.

As described above, when the freeze/recording switch provided in the operation section 6 is short pressed and the freeze processing is executed, an image at the time of the freeze processing being executed is transmitted from the endoscope apparatus 1 to the PC 32 or the mobile terminal 33. When the freeze processing is executed, it indicates that the examiner is interested in an image at that time, and the image recorded in the PC 32 or the mobile terminal 33 is an image required for subsequent detailed examination.

Therefore, by an endoscope system of the present embodiment, it is possible to transmit only necessary images, among images photographed by an endoscope apparatus, to a mobile device.

Since an image is transmitted to the PC 32 or the mobile terminal 33 only when the freeze processing is executed, as described above, it is easy for the examiner to examine images required for examination. Furthermore, since an image is transmitted to the PC 32 or the mobile terminal 33 only when the freeze processing is executed, a large capacity memory is not required on the PC 32 side or the mobile terminal 33 side.

Furthermore, in the present embodiment, when the freeze processing is executed, the image is not recorded in the endoscope apparatus 1 but transmitted to the PC 32 or the mobile terminal 33. Therefore, the endoscope apparatus 1 also is not required to be equipped with a large capacity memory.

Modification 1

When the freeze switch is pressed down, the endoscope apparatus 1 of the first embodiment does not store an image in the endoscope apparatus 1 but transmits the image to the PC 32 or the mobile terminal 33 which is a mobile device. When the freeze switch is pressed down, an endoscope apparatus 1 of a modification 1 transmits an image to the PC 32 or the mobile terminal 33, which is a mobile device, and stores the image in the endoscope apparatus 1.

Figure 4:
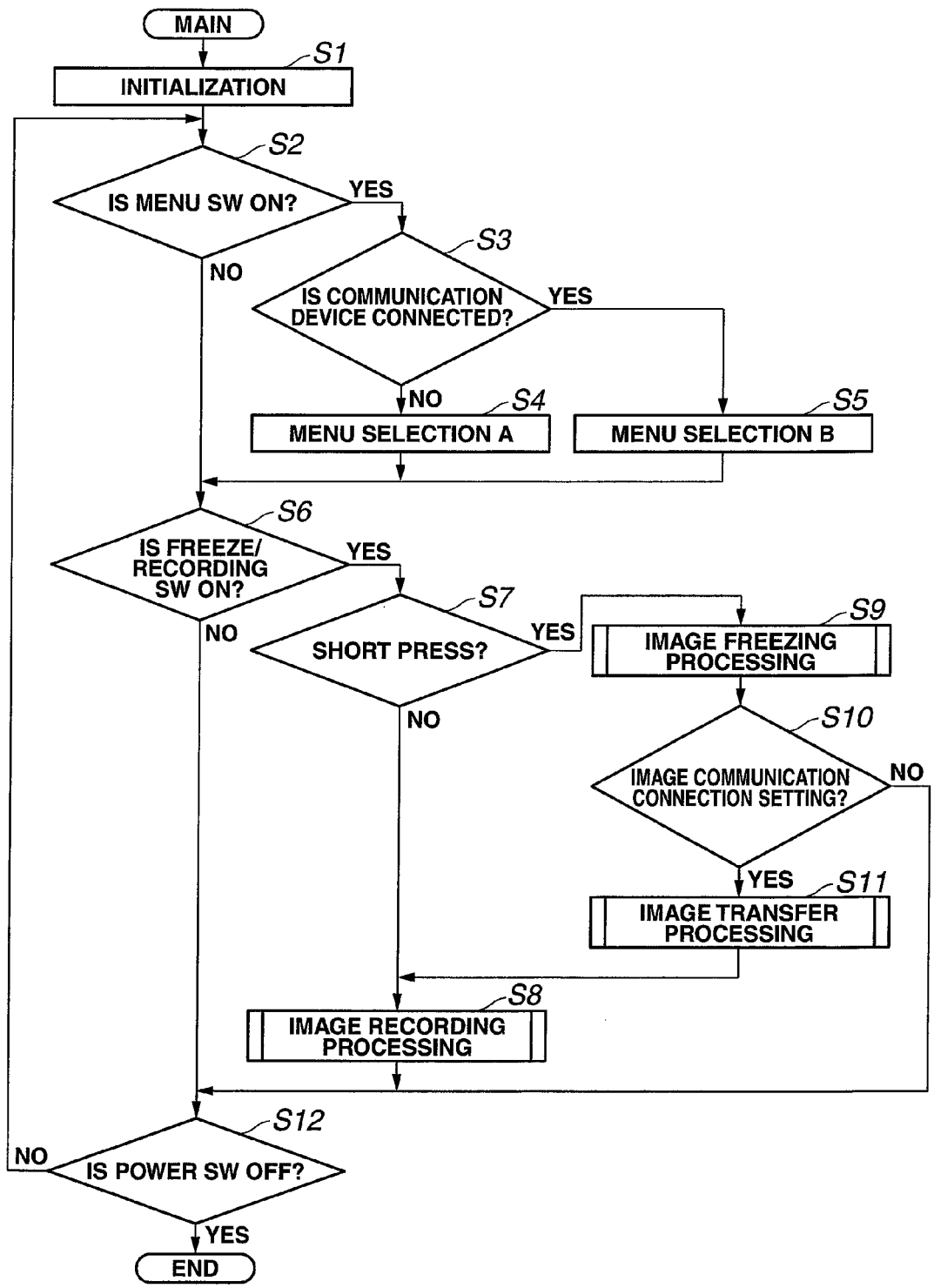
FIG. 4 is a flowchart showing an example of an operation of an endoscope apparatus 1 according to a modification 1 of the first embodiment.

FIG. 4 is a flowchart showing an example of an operation of the endoscope apparatus 1 according to the modification 1 of the first embodiment. Note that, in FIG. 4, processes similar to those in FIG. 3 are given the same reference numerals, and description thereof will be omitted.

When the image freeze processing is executed at step S9, and it is judged at step S10 that the image communication connection setting has been made, the CPU 16 executes the image transfer processing at step S11 and proceeds to step S8. Then, the CPU 16 executes the image recording processing at step S8 and judges whether the power switch is off or not at step S12. The other processes are similar to those of the first embodiment.

According to the above process, an image is stored in the endoscope apparatus 1, and the PC 32 or the mobile terminal 33 which is a receiving apparatus when the freeze processing is executed, and, therefore, the image can be backed up.

Modification 2

The endoscope apparatus 1 of the first embodiment transmits an image to the PC 32 or the mobile terminal 33 when the freeze switch is pressed down. An endoscope apparatus 1 of a modification 2 also transmits a still image to the PC 32 or the mobile terminal 33 when the still image is photographed. However, the image transfer processing for transmitting a moving image to the PC 32 or the mobile terminal 33 is inhibited because much power of the CPU 16 is spent during moving image photographing processing.

Figure 5:
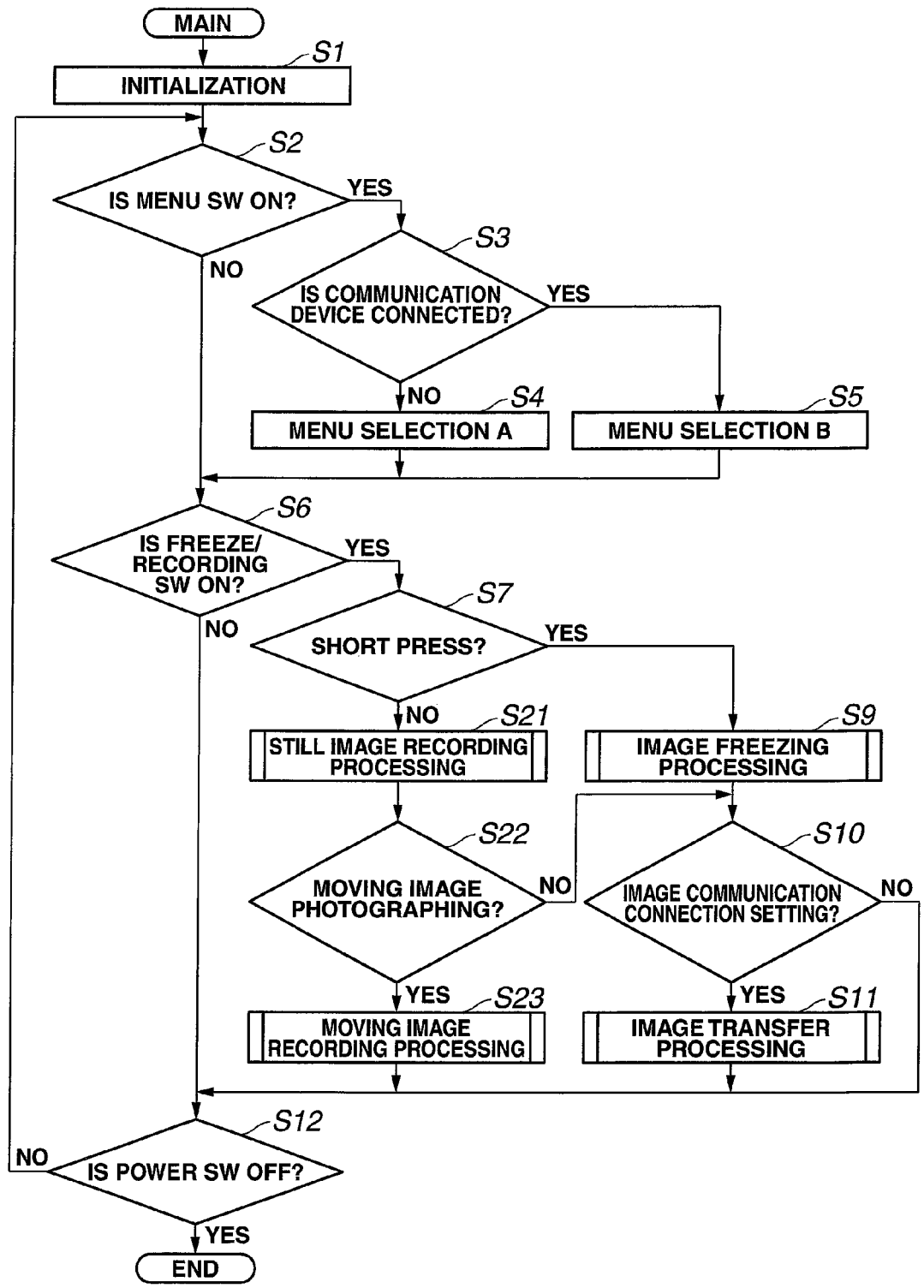
FIG. 5 is a flowchart showing an example of an operation of an endoscope apparatus 1 according to a modification 2 of the first embodiment.

FIG. 5 is a flowchart showing an example of an operation of the endoscope apparatus 1 according to the modification 2 of the first embodiment. Note that, in FIG. 5, processes similar to those in FIG. 3 are given the same reference numerals, and description thereof will be omitted.

If judging that the freeze/recording switch has not been short pressed, that is, the freeze/recording switch has been long pressed, at step S7, the CPU 16 executes the still image recording processing (step S21). Then, by detecting whether the freeze/recording switch is further long pressed or not, the CPU 16 judges whether moving image photographing is to be performed or not (step S22). If moving image photographing is not to be performed, the CPU 16 makes a judgment about the image communication connection setting at step S10. After that, if the image communication connection setting has been made, the CPU 16 executes the image transfer processing for transferring a recorded still image to the PC 32 or the mobile terminal 33, at step S11. On the other hand, if it is judged at step S22 that moving image photographing is to be performed, the CPU 16 executes the moving image recording processing (step S23), and the process proceeds to step S12.

According to the above process, when the freeze processing and the still image recording processing are executed, an image is transmitted to the PC 32 or the mobile terminal 33, and, when the moving image recording processing is being executed, transmission of an image to the PC 32 or the mobile terminal 33 is inhibited. Thus, when the moving image recording processing is being executed, processing on the endoscope apparatus 1 side is heavy, that is, the system is in a busy state, and, therefore, image transmission processing is inhibited while the moving image recording processing is being executed so that operability of the endoscope apparatus 1 is not damaged.

Modification 3

The endoscope apparatus 1 of the first embodiment transmits an image to the PC 32 or the mobile terminal 33 when the freeze switch is pressed down. An endoscope apparatus 1 of a modification 3 transmits an image to the PC 32 or the mobile terminal 33 when the freeze switch is pressed down and an operation of bending the bending section 22 is detected.

Figure 6:
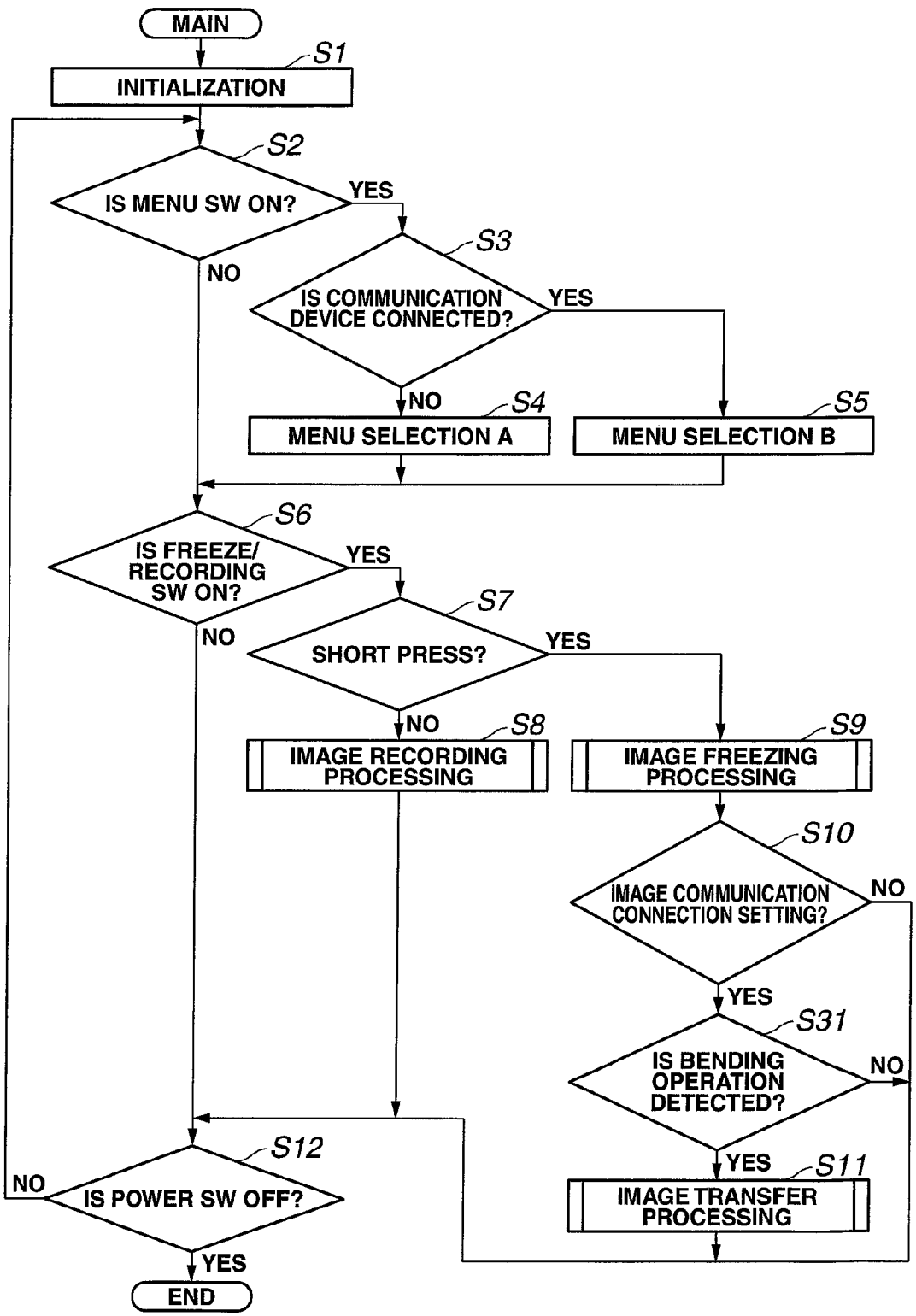
FIG. 6 is a flowchart showing an example of an operation of an endoscope apparatus 1 according to a modification 3 of the first embodiment.

FIG. 6 is a flowchart showing an example of an operation of the endoscope apparatus 1 according to the modification 3 of the first embodiment. Note that, in FIG. 6, processes similar to those in FIG. 3 are given the same reference numerals, and description thereof will be omitted.

When the image freeze processing is executed at step S9, and it is judged at step S10 that the image communication connection setting has been made, the CPU 16 monitors a signal inputted from the operation section 6 and judges whether the operation of bending the bending section 22 is performed or not (step S31). If the operation of bending the bending section 22 is performed, the CPU 16 executes the image transfer processing at step S11, and the process proceeds to step S12. If the operation of bending the bending section 22 is not performed, the process proceeds to step S12.

According to the above process, an image is transmitted to the PC 32 or the mobile terminal 33 only when the freeze/recording switch provided in the operation section 6 is short pressed to execute the freeze processing and the operation of bending the bending section 22 is specified. In general, when the operation of bending the bending section 22 is not specified, the possibility of case where the insertion section 20 is inserted in an object, for example, is strong. When the operation of bending the bending section 22 is specified, the possibility of a case of detailed examination being executed is strong. Therefore, there is a strong possibility that an image recorded in the PC 32 or the mobile terminal 33 is an image required for subsequent detailed examination, in comparison with the first embodiment.

Second Embodiment

Next, a second embodiment will be described.

Since an endoscope apparatus 1 of the second embodiment is configured similarly to the endoscope apparatus 1 of the first embodiment, description thereof will be omitted. The endoscope apparatus 1 of the first embodiment transmits an image to the PC 32 or the mobile terminal 33 when the freeze switch is pressed down. The endoscope apparatus 1 of the second embodiment collectively transmits images to the PC 32 or the mobile terminal 33.

Therefore, when an image transfer mode is set by the user, the CPU 16 creates an image transfer folder and changes setting for the created image transfer folder to a new folder. Then, after collectively recording photographed images to the new folder, the CPU 16 executes the image transfer processing.

Next, an operation of the endoscope apparatus 1 configured as described above will be described.

Figure 7:
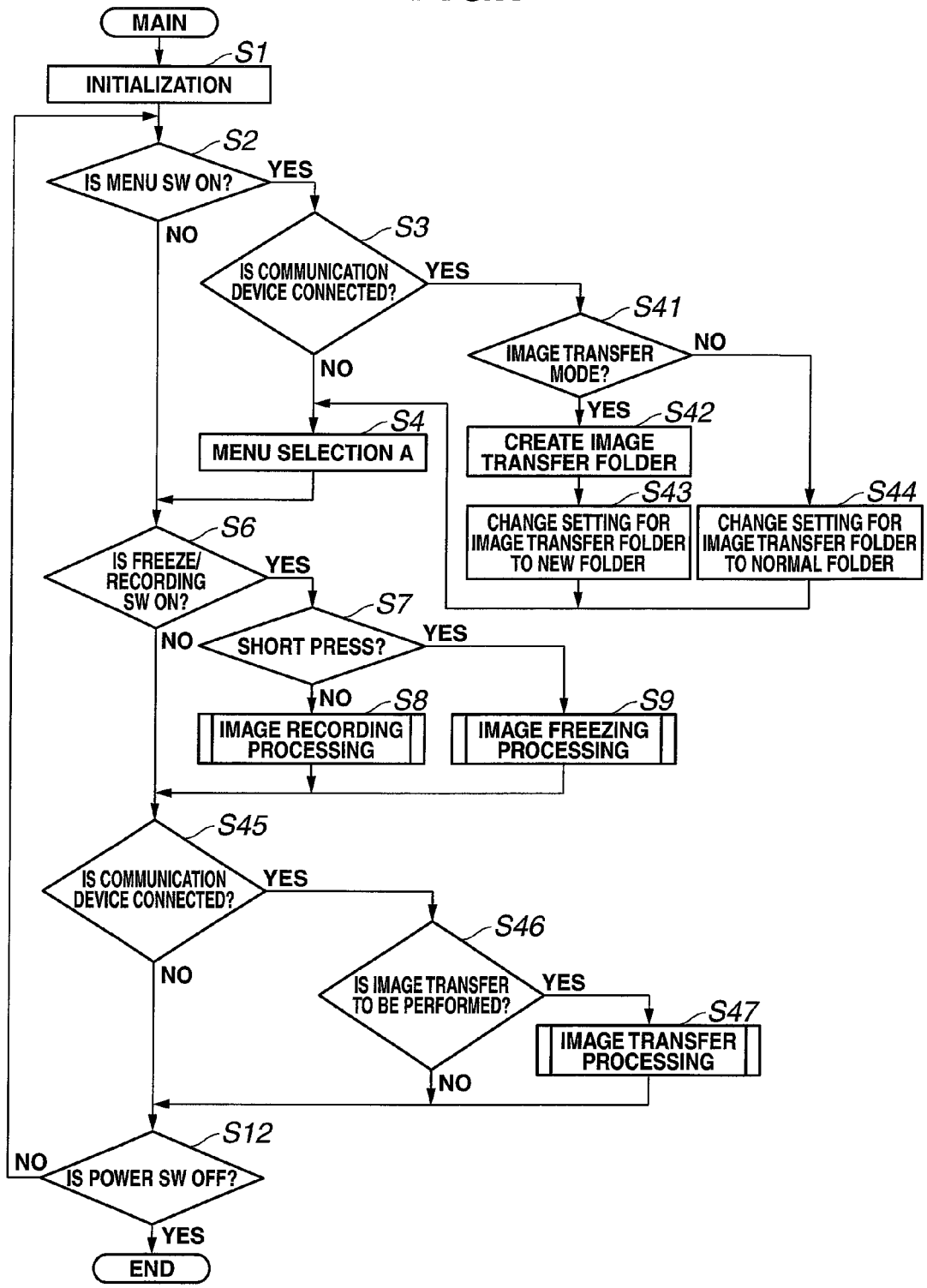
FIG. 7 is a flowchart showing an example of an operation of an endoscope apparatus 1 of a second embodiment.

FIG. 7 is a flowchart showing an example of the operation of the endoscope apparatus 1 of the second embodiment. Note that, in FIG. 7, processes similar to those in FIG. 3 are given the same reference numerals, and description thereof will be omitted. When it is judged at step S3 that a communication device is connected, the CPU 16 monitors a signal inputted from the operation section 6 and judges whether the image transfer mode is set or not (step S41). In the case of the image transfer mode (a first mode), more specifically, when a mode in which image transfer is not performed (a second mode) is changed to the image transfer mode (the first mode), the CPU 16 creates an image transfer folder (step S42). Then, the CPU 16 changes setting for the image storage folder to a new folder (step S43), and the process proceeds to step S4. On the other hand, if the image transfer mode is not set, more specifically, when the image transfer mode (the first mode) is changed to the mode in which image transfer is not performed (the second mode), the CPU 16 changes setting for the image storage folder to normal folder (step S44), and the process proceeds to step S4.

Then, when the image recording processing is executed at step S8, the CPU 16 records images to the new folder. In the recording processing, recording of images to the new folder is performed until the image transfer mode (the first mode) is changed to the mode in which image transfer is not performed (the second mode).

Then, the CPU 16 judges whether a communication device is connected or not (step S45). If a communication device is not connected, the process proceeds to step S12. On the other hand, if a communication device is connected, the CPU 16 monitors a signal inputted from the operation section 6 and judges whether or not to perform image transfer (step S46). In this case, display for asking the user whether or not to perform image transfer to the monitor 4 is shown on the monitor 4, and whether or not to perform image transfer is determined by the user operating the operation section 6. Note that, for example, image transfer may be automatically performed when a predetermined volume of images has been recorded to the new folder.

If image transfer is not performed at step S46, the process proceeds to step S12. On the other hand, if image transfer is performed at step S46, the CPU 16 performs image transfer processing for transmitting the new folder in which the images are recorded, to the PC 32 or the mobile terminal 33 (step S47), and the process proceeds to step S12.

According to the above process, the endoscope apparatus 1 collectively transmits images which have been recorded for each folder by the image recording processing being executed, to the PC 32 or the mobile terminal 33, and, therefore, it is possible to facilitate management of images in the PC 32 or the mobile terminal 33.

Modification 1

The endoscope apparatus 1 of the second embodiment records an image to a new folder when the freeze/recording switch is pressed down. An endoscope apparatus 1 of a modification 1 records an image to a new folder when the freeze/recording switch is pressed down and the operation of bending the bending section 22 is detected.

Figure 8:
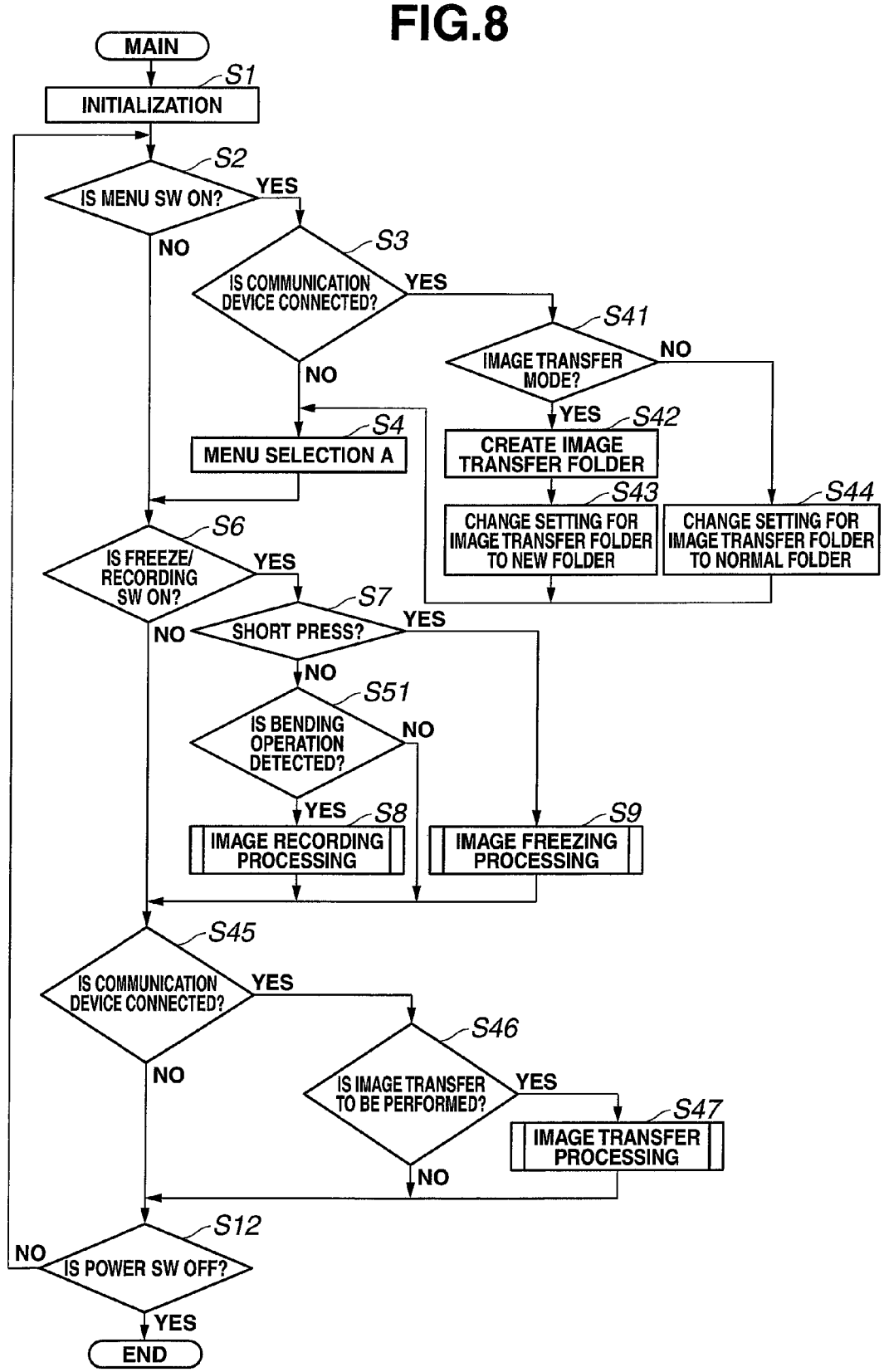
FIG. 8 is a flowchart showing an example of an operation of an endoscope apparatus 1 according to a modification 1 of the second embodiment.

FIG. 8 is a flowchart showing an example of an operation of the endoscope apparatus 1 according to the modification 1 of the second embodiment. Note that, in FIG. 8, processes similar to those in FIG. 7 are given the same reference numerals, and description thereof will be omitted.

When the freeze/recording switch is not short pressed at step S7, the CPU 16 monitors a signal inputted from the operation section 6 and judges whether the operation of bending the bending section 22 is performed or not (step S51). If the operation of bending the bending section 22 is performed, the CPU 16 executes the image recording processing at step S8, and the process proceeds to step S45. On the other hand, if the operation of bending the bending section 22 is not performed, the image recording processing is not performed, and the process proceeds to step S12.

According to the above process, an image at time when the image recording processing is executed, and the operation of bending the bending section 22 is specified is recorded to a folder, and images are collectively transmitted to the PC 32 or the mobile terminal 33, and, therefore, it is possible to facilitate management of images in the PC 32 or the mobile terminal 33 and to transmit only images required for examination.

Modification 2

An endoscope apparatus 1 of a modification 2 of the second embodiment newly creates transferred images after the image transfer processing at step S47 in FIG. 8 and gives image transfer completion information indicating that image transfer has been executed, to the created images.

Figure 9:
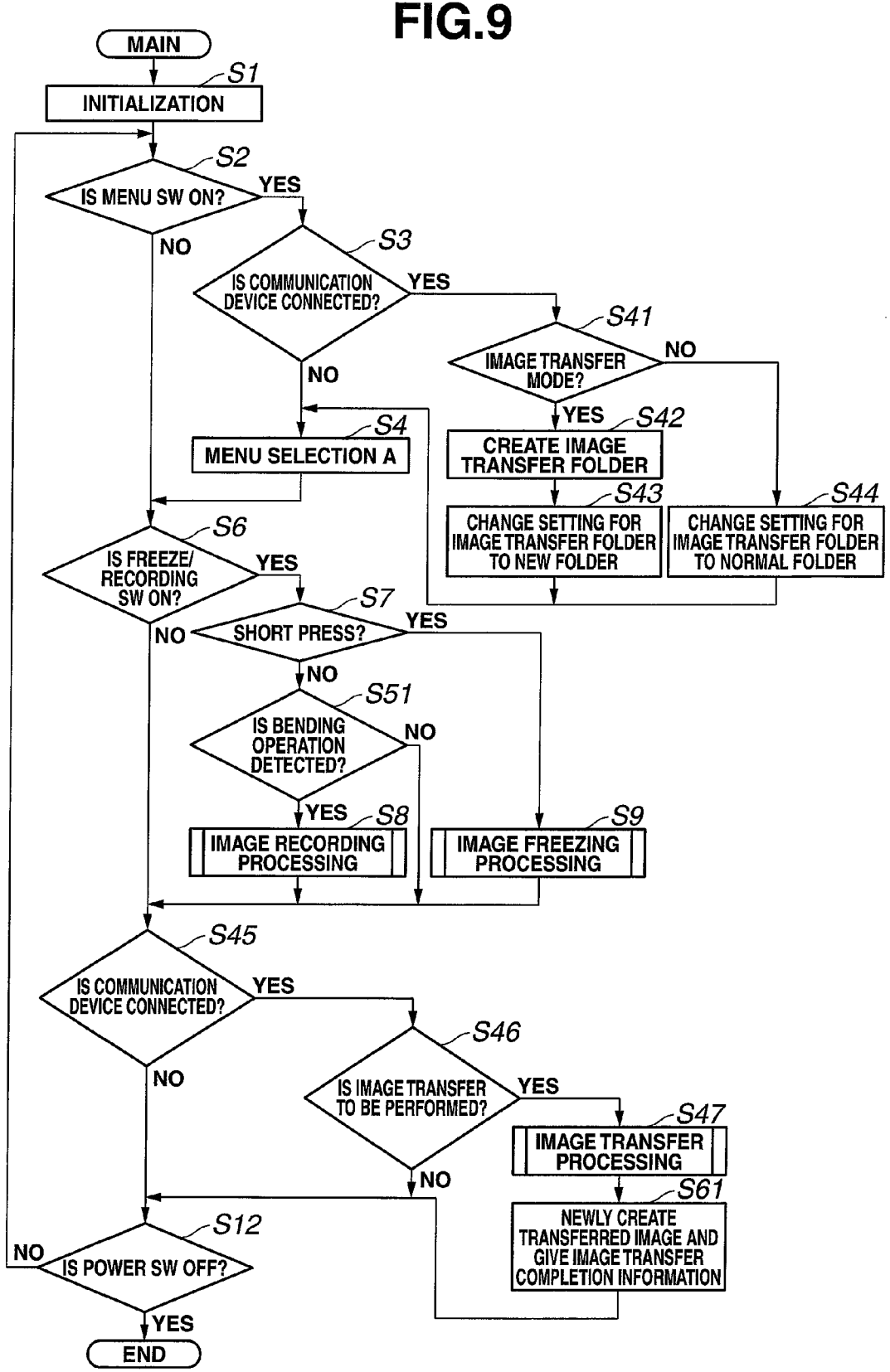
FIG. 9 is a flowchart showing an example of an operation of an endoscope apparatus 1 according to a modification 2 of the second embodiment.

FIG. 9 is a flowchart showing an example of an operation of the endoscope apparatus 1 according to the modification 2 of the second embodiment. Note that, in FIG. 9, processes similar to those in FIG. 8 are given the same reference numerals, and description thereof will be omitted.

When it is judged at step S46 that image transfer is to be performed, and the image transfer processing is executed at step S47, images which have been image-transferred are newly created, and image transfer completion information is given to the newly created images (step S61). Then, the processing of step S61 is executed, the process proceeds to step S12.

Giving of the image transfer completion information is realized by adding a predetermined character string, for example, a character string of "_a" to the end of a filename of an image file in which the newly created images are recorded. For example, respective images with filenames of "xxxx" and "yyyy" are transferred, the character string "_a" is added to the end of the filenames of the image files, and the filenames become "xxxx_a" and "yyyy_a", respectively.

Giving of the image transfer completion information may be realized by storing the image transfer completion information in the image file of the newly created images.

Figure 10:
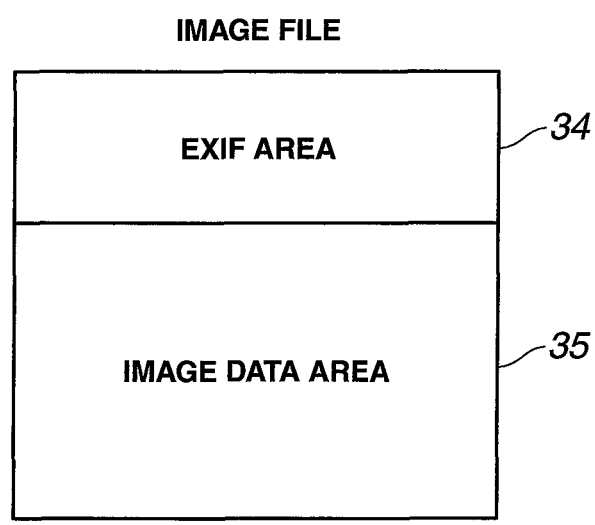
FIG. 10 is a diagram showing a data structure of an image file.

FIG. 10 is a diagram showing a data structure of the image file. As shown in FIG. 10, the image file is configured by an EXIF area 34 in which predetermined data can be stored and an image data area 35 in which image data is stored. When the image transfer processing is executed, the image transfer completion information is stored in the EXIF area 34.

Note that, though giving of the image transfer completion information is executed after the image transfer processing of step S47 in FIG. 8, it is not limited thereto and may be executed after the image transfer processing of step S11 in FIG. 3 or after the image transfer processing of step S47 in FIG. 7.

According to the above process, the examiner can easily grasp images transmitted to the PC 32 or the mobile terminal 33 which is a receiving apparatus among images stored in the endoscope apparatus 1.

Note that, as for respective steps in flowcharts in the present specification, execution order of the steps may be changed; multiple steps may be executed at the same time; or the steps may be executed in a different order at each execution, unless contrary to the nature thereof.

The present invention is not limited to the embodiments and modifications described above, and various changes, alterations and the like can be made within a scope not departing from the spirit of the present invention.

What is claimed is:

1. An endoscope system comprising:
   an endoscope apparatus capable of recording a picked-up endoscopic image;
   a communication device that transmits the picked-up endoscopic image; and
   a mobile device having a function of communicating with the communication device and recording the endoscopic image transmitted from the communication device;
   wherein:
   the endoscope apparatus and the mobile device are connected via wireless communication;
   the endoscope apparatus transmits the endoscopic image from the endoscope apparatus to the mobile device when freeze processing is executed; and
   the endoscope apparatus comprises:
   (i) a freeze processing judging section that judges whether or not an instruction to execute freeze processing is received;
   (ii) a freeze processing executing section that executes freeze processing of the image if the freeze processing judging section judges that the instruction to execute freeze processing is received; and
   (iii) an image transfer processing section that automatically transfers, via the communication device, the frozen image to the mobile device, immediately after execution of the freeze processing by the freeze processing executing section, and
   wherein the endoscope apparatus transmits the endoscopic image to the mobile device only at a time when the freeze processing is executed and an operation of bending a bending section provided in an insertion section is detected.

2. The endoscope system according to claim 1, wherein the endoscopic image is recorded in the endoscope apparatus when the freeze processing is executed.

3. The endoscope system according to claim 1, wherein the endoscopic image is not recorded in the endoscope apparatus when the freeze processing is executed.

4. The endoscope system according to claim 1, wherein transmission of the endoscopic image to the mobile device is inhibited while moving image photographing processing is being executed in the endoscope apparatus.

5. An endoscope system comprising:
   an endoscope apparatus capable of recording a picked-up endoscopic image;
   a communication device that transmits the picked-up endoscopic image; and
   a mobile device having a function of communicating with the communication device and recording the endoscopic image transmitted from the communication device;
   wherein:
   the endoscope apparatus and the mobile device are connected via wireless communication;
   the endoscope apparatus is selectively operable in a first mode of transmitting the endoscopic image to the mobile device and a second mode of not transmitting the endoscopic image to the mobile device, and
   the endoscope apparatus comprises:
   (i) an image transfer mode setting section that sets one of the first mode and the second mode;
   (ii) an image transfer folder creating section that creates an image transfer folder for storing the endoscopic image, in response to the image transfer mode setting section setting the first mode;
   (iii) a transferred image recording section that stores picked-up endoscopic images in the image transfer folder until the first mode is changed to the second mode; and (iv) an image transfer processing section that transfers, via the communication device, the image transfer folder to the mobile device, wherein the endoscope apparatus stores the endoscopic image only at a time when an operation of bending a bending section provided in an insertion section is detected in the folder.

6. The endoscope system according to claim 5, wherein, upon transmitting the endoscopic image to the mobile device in the first mode, the endoscope apparatus newly creates the transmitted endoscopic image and adds image transmission completion information to the newly created endoscopic image.

* * * * *